US012678320B2

(12) United States Patent
Rafiqpoor

(10) Patent No.: US 12,678,320 B2
(45) Date of Patent: ***Jul. 14, 2026

(54) VENTILATION ASSISTANCE DEVICE

(71) Applicant: LMA OPTIMIZER B.V., Maastricht (NL)

(72) Inventor: Khaled Rafiqpoor, Maastricht (NL)

(73) Assignee: LMA OPTIMIZER B.V., Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 19/146,174

(22) PCT Filed: Jan. 9, 2024

(86) PCT No.: PCT/EP2024/050412
§ 371 (c)(1),
(2) Date: Jul. 7, 2025

(87) PCT Pub. No.: WO2024/149770
PCT Pub. Date: Jul. 18, 2024

(65) Prior Publication Data
US 2026/0108373 A1      Apr. 23, 2026

(30) Foreign Application Priority Data
Jan. 10, 2023      (EP) ..................................... 23150956

(51) Int. Cl.
*A61F 5/058*          (2006.01)
*A61M 16/04*         (2006.01)
(52) U.S. Cl.
CPC ..... *A61F 5/05891* (2013.01); *A61M 16/0447* (2014.02); *A61M 2205/42* (2013.01)
(58) Field of Classification Search
CPC .. A61F 5/05891; A61F 5/05883; A61F 5/058; A61F 5/05; A61F 5/04; A61F 5/01;
(Continued)

(56) References Cited

U.S. PATENT DOCUMENTS 1,990,411 A  *  2/1935  Lowry ...................... A61F 5/56
24/200
5,249,571 A    10/1993  Brain
(Continued)

FOREIGN PATENT DOCUMENTS

CN      103357096 A1    10/2013
CN      108378966 A      8/2018
(Continued)

OTHER PUBLICATIONS

Non final office action for coressponding U.S. Appl. No. 17/642,063; dated Aug. 12, 2025 (26 pages).
(Continued)

*Primary Examiner* — Tarla R Patel
(74) *Attorney, Agent, or Firm* — Mendelsohn Dunleavy, PC; Kevin J. Dunleavy

(57)                ABSTRACT

A ventilation assembly (37) for use in ventilation of a subject using a laryngeal mask (5) comprises a head-wearable harness (39) and a pusher (41). The harness is arrangeable on the subject's head (H) for supporting the pusher to press against the floor of the mouth (15) of the subject (P). The pusher comprises laterally opposite protrusions to displace, in use and operably supported by the harness on the subject (P), soft tissue of the subject at the left and right submandibular triangles (trigonum submandibulare) in cranial direction relative to the mandible (29) of the subject and surrounding tissue of the subject such as the submental triangle (trigonum submentale) for, when the laryngeal mask is installed in the airway of the subject, urging internal soft tissue of the subject against the laryngeal mask in the airway of the subject. Each protrusion or the pusher as a whole is hollow providing a recess for accommodating an operators' finger.

13 Claims, 9 Drawing Sheets

(58) Field of Classification Search

CPC . A61F 5/00; A61M 16/0447; A61M 2205/42; A61M 16/0445; A61M 16/0434; A61M 16/04; A61M 16/00

See application file for complete search history.

(56) References Cited

U.S. PATENT DOCUMENTS

| | | | |
|---|---|---|---|
| 6,016,807 A * | 1/2000 | Lodge | A61F 13/12 128/848 |
| 7,047,977 B2 | 5/2006 | Frank | |
| 7,124,758 B1 | 10/2006 | Frank | |
| 8,695,607 B2 | 4/2014 | Hohenhorst | |
| 8,851,078 B2 * | 10/2014 | Newman | A61M 16/0683 128/207.11 |
| 2005/0247309 A1 | 11/2005 | Reddick | |
| 2007/0079832 A1 * | 4/2007 | Baldauf | A61M 25/02 128/201.22 |
| 2007/0181135 A1 | 8/2007 | Baker | |
| 2008/0163875 A1 * | 7/2008 | Aarestad | A61F 5/56 128/846 |
| 2008/0223377 A1 | 9/2008 | Kussick | |
| 2009/0095309 A1 | 4/2009 | Derrick et al. | |
| 2010/0294284 A1 | 11/2010 | Hohenhorst et al. | |
| 2012/0234330 A1 | 9/2012 | Saiz | |
| 2015/0164726 A1 | 6/2015 | Ward et al. | |
| 2018/0008452 A1 | 1/2018 | Wade | |
| 2024/0058559 A1 | 2/2024 | Rafiqpoor | |

FOREIGN PATENT DOCUMENTS

| | | | | |
|---|---|---|---|---|
| CN | 109640896 A | 4/2019 | | |
| CN | 208959050 U | 6/2019 | | |
| DE | 102005025996 B3 | 6/2005 | | |
| EP | 1981431 B1 | 7/2014 | | |
| GB | 2267034 A | 11/1993 | | |
| WO | 2009129081 A1 | 10/2009 | | |
| WO | WO-2010068251 A1 * | 6/2010 | ............ | A61F 5/055 |
| WO | 2012024728 A1 | 3/2012 | | |
| WO | 2021049941 A1 | 3/2021 | | |

OTHER PUBLICATIONS

Office action for corresponding Chinese application No. 202480006727.2; dated Jan. 27, 2026 (14 pages). Machine Translation.

International Search Report and Written Opinion for corresponding International application No. PCT/NL2020/050567; dated Dec. 3, 2020 (16 pages).

First Examination Report for corresponding Chinese application No. 202080064731.6; dated Aug. 7, 2024 (12 pages) Machine Translation.

Communication under Rule 71(3) issued in corresponding European patent application No. 20 775 432.6-1122; dated Nov. 12, 2024 (6 pages).

International Search Report and Written Opinion for corresponding International application No. PCT/EP2024/050412; Mar. 19, 2024 (19 pages).

International Preliminary Report on Patentability for corresponding International Application No. PCT/EP2024/050412; dated Apr. 4, 2025 (12 pages).

* cited by examiner

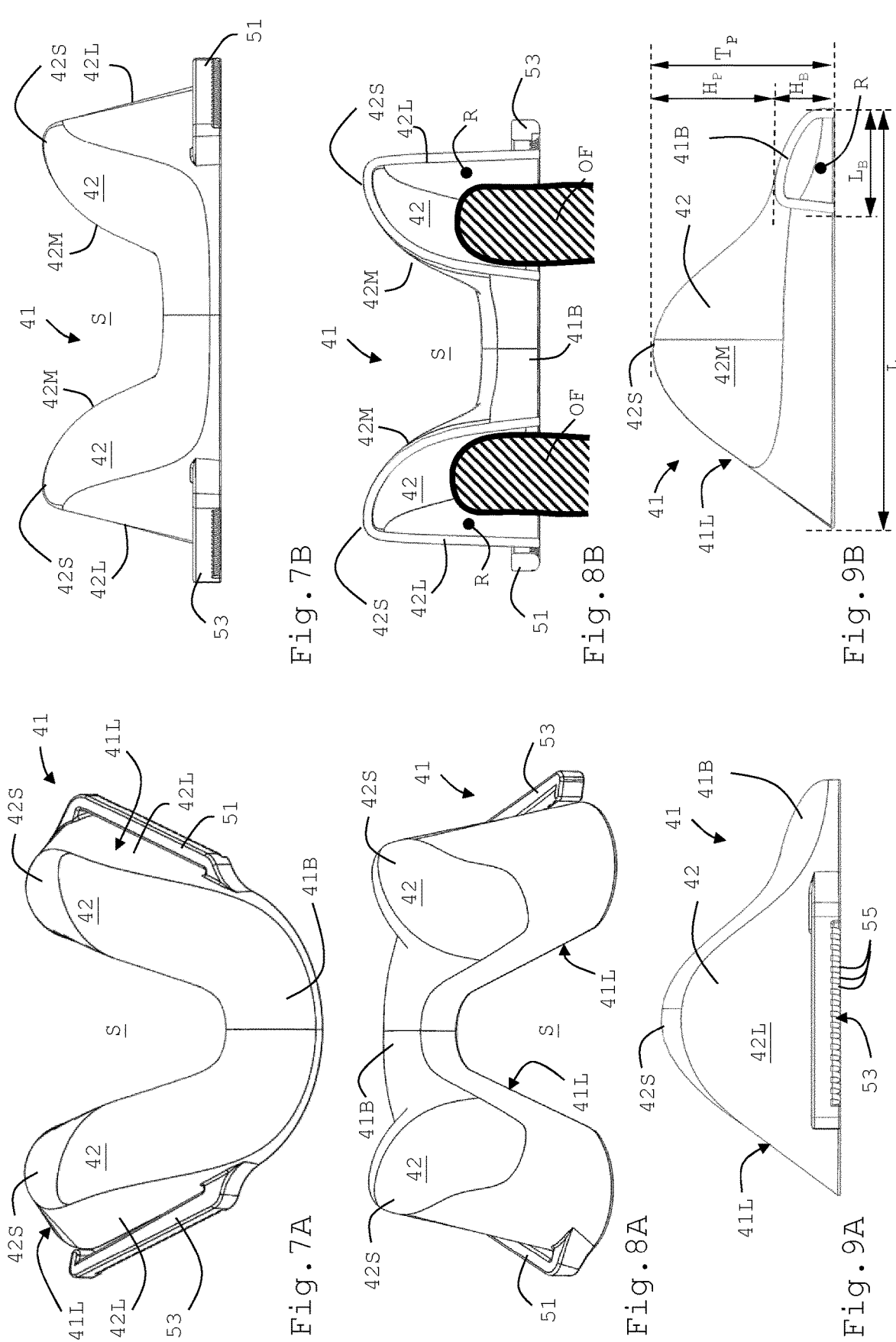

VENTILATION ASSISTANCE DEVICE

TECHNICAL FIELD

The present disclosure relates to a head wearable harness, and in particular to a head wearable harness for use in medical procedures where a laryngeal mask is used for ventilation of a subject.

BACKGROUND

Subjects incapable of normal breathing, e.g. when injured and/or sedated, may be subject to mechanical ventilation. Intubation is a well-known forced ventilation technique. The use of a laryngeal mask for forced ventilation is also well established and it is generally preferred over intubation as less invasive. Various (aspects of) laryngeal masks are disclosed in e.g. WO 2012/024728. Although laryngeal masks have been developed to effectively seal against the larynx, such sealing may not be perfect and leakages of air do still persist, for example, due to differences in a patient's anatomy relative to available mask shapes and sizes. Leakages may be due or worsened by sedation and muscle relaxation. Such leakages may affect control of amounts of ventilated air and/or control of a composition of ventilation air mixtures, which may e.g. contain one or more of moisture, sedatives, diagnostic substances and/or medicaments relative to ambient air. Such leakages should therefore be prevented.

In practice, in case leakages of a laryngeal masks are found and persist, possibly after repeated reapplication, practitioners tend to use a laryngeal mask of a bigger size, i.e. size up. However, if leakages even then still persist and/or if such larger laryngeal mask does not fit, intubation is used after all.

It is therefore desired to prevent such leakages and/or to increase the possibility of effective usage of laryngeal masks.

GB 2 267 034 discloses a laryngeal airway clamp, wherein a laryngeal mask airway device is clamped in position by a clamping member engaging the neck of a patient in opposition to the laryngeal mask of the device. The clamp engaging the neck presses against the airway and part of the clamp extends into the mouth and larynx of the patient which may interfere with access to the airway and/or with treatment of the patient.

It is further noted that several devices are known for establishing and maintaining the lower jaw or mandible of a subject in a desired position relative to the upper jaw but unrelated to and/or incompatible with laryngeal masks (see also below). E.g. US 2018/0008452 relates to a device to urge the mouth closed during sleep to reduce snoring and/or treat sleep disorders such as sleep apnea. In one aspect, the device includes a jaw-blocking object that is secured beneath the chin of a user and also contacting the clavicular region of the upper chest area. In another aspect, a device of the invention includes a jaw-blocking object in combination with a Continuous Positive Airway Pressure (CPAP) mask and headgear for use with a CPAP system. The CPAP mask is worn on the face of the user, thus being in contrast to a laryngeal mask which is inserted into the larynx of the user.

It is noted that several devices are known for establishing and maintaining the lower jaw or mandible of a subject in a desired position relative to the upper jaw, which all are configured and destined to overcoming obstructions of the airway, rather than urging the airway closed for sealing against a laryngeal mask as explained above. Such devices are therefore not related to use with forced ventilation.

E.g., US 2005/0247309 and US 2009/0095309 disclose rigid support devices for thrusting the jaw of a patient forwardly from the patient's chest to permit the patient to breathe freely during sedation or sleeping. Their operation depends on the patient's posture and (im-)mobility.

US 2010/0294284 discloses apparatus, systems, and methods which constrain and/or support tissue structures along an airway by wearing a support collar. A collar hinders access to the throat and/or restricts the wearer's mobility.

US 2007/0079832, and US 2015/0164726 are frames mounted near the patient's head for assisting respiration of a patient. The devices are configured for thrusting the jaw of a patient forwardly to permit the patient to breath freely during sedation or sleeping.

U.S. Pat. No. 7,124,758 discloses a device for treating snoring and obstructive sleep apnea. The device of U.S. Pat. No. 7,124,758 comprises a headband and two belts. The headband is placed on the head of a user and the belts are attached to the front of the headband, the belts are crossed over the top of the users head and then are made to go from the back of the users neck to cross under the users chin and then to attach to the front part of the headband. The device, in use, maintains sufficient tension to keep the jaws of the user locked together and the front teeth of the lower jaw in contact with the front teeth of the upper jaw and overcomes obstructions of the airway so that obstructive sleep apnea is relieved and associated morbidity is reduced.

U.S. Pat. No. 7,047,977 teaches a medical device for overcoming airway obstruction by the tongue of a sedated or unconscious patient lying in the supine position.

WO 2021/049941 discloses a ventilation assembly (37) for use in ventilation of a subject using a laryngeal mask (5) comprises a head-wearable harness (39) and a pusher (41). The harness is arrangeable on the subject's head (H) for supporting the pusher against the floor of the mouth (15) of the subject (P). The pusher is arranged to displace soft tissue of the floor of the mouth in cranial direction relative to the mandible (29) of the subject for, when the laryngeal mask is installed in the airway of the subject, urging internal soft tissue of the subject against the laryngeal mask in the airway of the subject.

Although working admirably, further improvements to such assembly are desired.

SUMMARY

In view of the above, a ventilation assembly and a head wearable harness as specified herein are provided.

In particular is provided ventilation assembly for use in ventilation of a subject using a laryngeal mask comprising a head-wearable harness and a pusher. The harness is arrangeable on the subject's head for supporting the pusher to press against the floor of the mouth of the subject. The pusher comprises laterally opposite protrusions to displace, in use and operably supported by the harness on the subject, soft tissue of the subject at the left and right submandibular triangles (trigonum submandibulare) in cranial direction relative to the mandible of the subject and surrounding tissue of the subject such as the submental triangle (trigonum submentale) for, when the laryngeal mask is installed in the airway of the subject, urging internal soft tissue of the subject against the laryngeal mask in the airway of the subject. Each protrusion, is hollow providing a recess for accommodating an operators' finger.

This facilitates manipulation and placement of the pusher. Care givers like doctors and nurses are trained in providing care to a subject based on touch and bio feedback; by placing one or more fingers in the protrusions, the care giver can arrange the pusher in an appropriate position on, and adjust pressure to, the floor of the subject's mouth for displacing the internal soft tissue of the floor of the mouth of the subject. This is in particular facilitated if the recesses are provided in a bottom (in use: caudal) side of the pusher.

The pusher may generally be U-shaped in transverse direction, comprising a bridge in a front (in use: ventral) portion for, in use and operably supported by the harness on the subject, accommodating the subject's tissue at the submental triangle (trigonum submentale) and laterally opposing legs (41L) extending rearward (in use: dorsal) from the bridge in a rear (in use: dorsal) portion and comprising the laterally opposing protrusions.

This may facilitate placement and/or orienting the pusher and the protrusions relative to the mandible.

The pusher may be formed as a continuous hollow body, e.g. a shell and/or monocoque. This may provide a robust pusher which may resist deformation and/or it may facilitate manufacturing the pusher, e.g. by moulding techniques and/or plate forming techniques.

The pusher may have a substantially constant thickness in a direction normal to a pusher outside surface. This may facilitate positioning the pusher and/or improve biofeedback to a care giver, by facilitating "feeling through the pusher" the subject and/or providing a constant distance between care givers' finger(s) on one side of the pusher and the subject and the subject's anatomy of the subject on an opposite side of the pusher's thickness, without varying separation between the care givers' finger(s) and the subject/subject's features due to a varying pusher thickness.

The bridge and protrusions may provide a substantially continuously smooth outer (subject-facing/subject-contacting, in use) surface, the bridge having a saddle shape, assisting prevention of local pressure changes and in particular elevated pressures which may harm the subject's skin and/or tissue underneath (e.g. providing an excess local pressure reducing or blocking blood flow). The surface may be closed or comprise, at least partly, openings which may help oxygenating the subject's skin and/or reducing moisture build-up.

The protrusions may have a summit in a range arranged from a rear end of the pusher, in use, in a position between about ⅓ and ½ of a pusher length, in particular between ⅖ and ½ of the pusher length.

The bridge may extend for about ⅓ to ¼ from a front end of the pusher. The protrusions, in particular the summits thereof, may be arranged dorsal of the bridge.

The protrusions may provide a space between them having a shape generally flaring in cranial direction in use, preferably a symmetric shape. The shape may be flaring in a sagittal plane but also in other directions, associated with a smooth curvature of the protrusions. This may help appropriately position the protrusions, e.g. helping centering of the pusher relative to the floor of the mouth. Also or alternatively the space may accommodate subject's tissue; the flaring shape may help guide the tissue and prevent excess and/or asymmetric pressure.

Each protrusion may have a base and each protrusion having a summit may be arranged laterally outward on the respective base, being arranged in a lateral outer half of the base (as seen in main axial direction), in particular within about ¼ of the sagittal cross sectional width of the base or less, preferably in a range of about ⅕ to ⅒ of the sagittal cross sectional width of the base. A leg of a U-shaped pusher may define the base and a width of the leg may define the width of the base. This may fortify the protrusion and/or may provide for localising at least the summit of the protrusion relatively laterally outward on the base for localising the applied force to, and displacement of soft tissue of, the subjects' submental triangles.

The pusher may comprise one or more connectors, for operably connecting the harness and the pusher, preferably at least partly reversibly connecting the harness and the pusher. This may facilitate one or more of manufacturing, transporting, storing, preferably cleaning (e.g. disinfecting and/or sterilizing the harness and the pusher separately). Also or alternatively, reversibly connecting the harness and the pusher may facilitate (preferably repeatedly) connecting and disconnecting the pusher and the harness, which may facilitate placing and/or adjusting the pusher and/or the assembly as a whole on the subject and removing it from the subject.

The one or more connectors may comprise at least one hook and/or at least one loop for operably engaging the harness. The hook and/or loop may be provided with a localising structure for at least part of the harness such as a surface portion that is at least one of providing elevated friction with the harness, being corrugated and being toothed. A surface portion that provides elevated friction with the harness may comprise one or more of a roughened surface portion, a rubberised portion and/or a portion interacting with at least part of the harness such as entangling at least part of the harness and/or clamping onto the harness. Each connector preferably defines. Each leg may be provided with at least one of the one or more connectors.

The harness may be attachable or attached, e.g. by at least one of the one or more connectors discussed above, to be at least in use arranged laterally adjacent the summit of a/each protrusion and preferably for connecting and fixing the harness to the pusher substantially symmetric with respect to a sagittal plane through the summit of the respective laterally adjacent protrusion.

This may facilitate arranging and/or maintaining the pusher, the harness, and the subject in a suitable relative position and/or orientation. Also or alternatively it may facilitate providing a suitable force direction to urge the internal soft tissue of the subject against the laryngeal mask in the airway of the subject.

The harness may comprise or be a flexible band, in particular providing a widened cranial portion. Also or alternatively, the harness may comprise an elastic portion and/or a substantially inelastic portion, either or both of which may assist adjusting force and/or pressure of the pusher to the subject.

The assembly may comprise one or more sound mufflers and/or sound emitters for controlling sound to an ear of the subject, which may be attached to the harness. This may assist damping and/or masking noises from an environment to the subject, e.g. from one or more of an operating theatre, a surgical procedure, a therapeutic ward, etc. This may prevent auditory information reaching the subject, e.g. unpleasant sounds, and/or administrating pleasant sounds to the subject. The harness may in use, extend over an ear of the subject, which may facilitate positioning the one or more sound mufflers and/or sound emitters.

The assembly may comprise a laryngeal mask.

Further, associated with the disclosure above and any benefits discussed herein, a method of ventilating a subject is provided, comprising:

operably installing a laryngeal mask in the airway of the subject; and providing the subject with a ventilation assembly as discussed herein, and arranging the pusher to displace the soft tissue of the floor of the mouth of the subject in cranial direction of the subject to urge internal soft tissue of the subject against the laryngeal mask in the airway of the subject for at least partly sealing the airway and preventing leaks along the laryngeal mask by urging soft tissue of the floor of the mouth of the subject in a cranial direction of the subject relative to the mandible of the subject.

The method may comprise operably installing a laryngeal mask in the airway of the subject; operably arranging the pusher on the floor of the subject's mouth by hand and controlling sealing of the airway; and fixing the pusher to the subject by connecting at least part of the harness to the pusher.

BRIEF DESCRIPTION OF THE DRAWINGS

The above-described aspects will hereafter be more explained with further details and benefits with reference to the drawings showing a number of embodiments by way of example.

FIG. 7A is front view along a sagittal from above;

FIG. 7B is a front view along a sagittal plane;

FIG. 8A is a rear view along a sagittal from above;

FIG. 8B is a cross section view to a coronal cross section plane as indicated in FIGS. 6A, 6B with VIII;

FIG. 9A is a lateral side view of the pusher;

FIG. 9B is a cross section view to a sagittal cross section plane as indicated in FIGS. 6A, 6B with IX;

DETAILED DESCRIPTION OF EMBODIMENTS

Figure 1A:
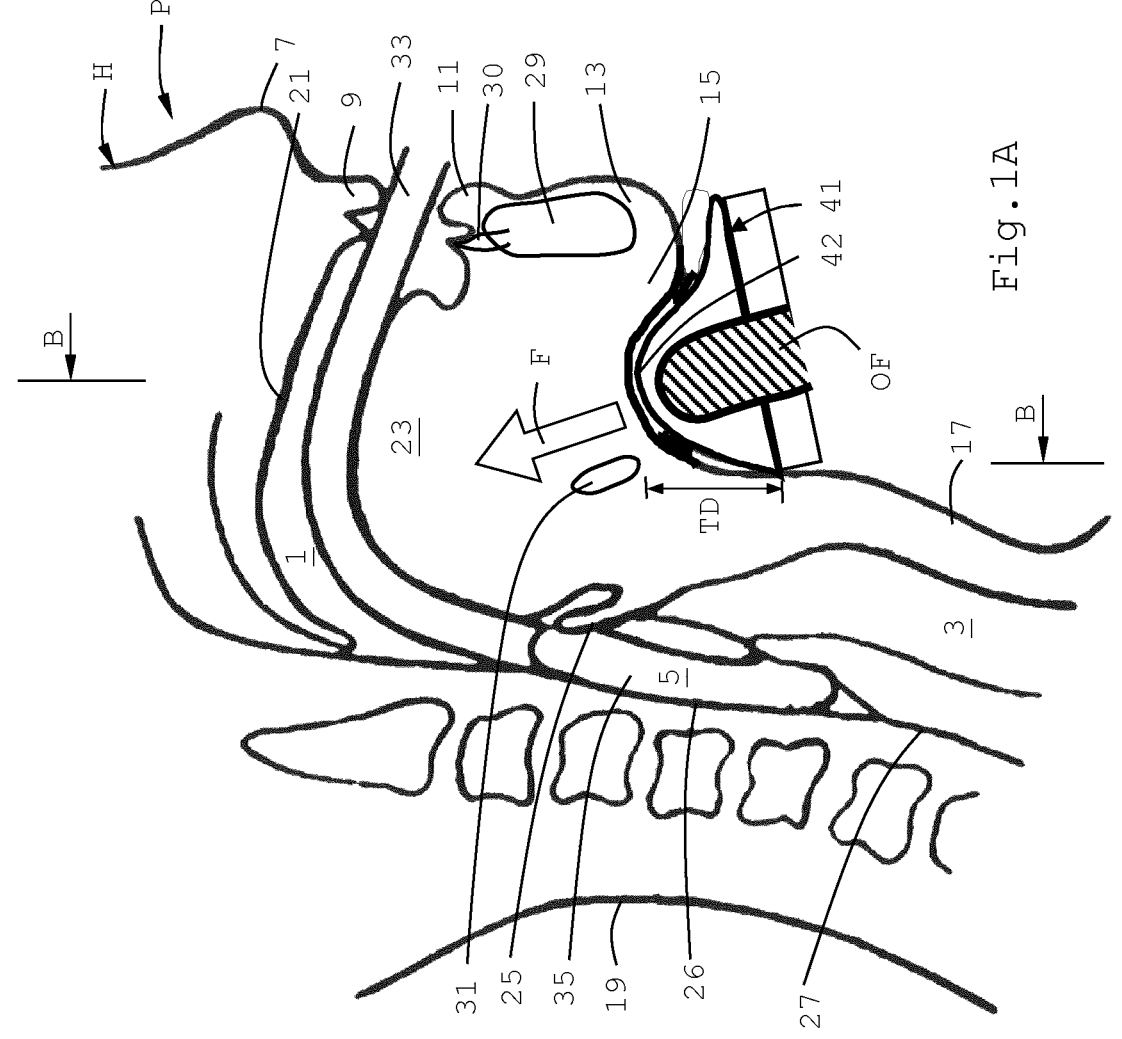
FIG. 1A is a partial schematic cross section of a human neck area with a laryngeal mask inserted in operative position, also including part of a ventilation assembly as disclosed herein.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where helpful individualised with alphabetic suffixes.

Further, unless otherwise specified, terms like "detachable" and "removably connected" are intended to mean that respective parts may be disconnected essentially without damage or destruction of either part, e.g. excluding structures in which the parts are integral (e.g. welded or moulded as one piece), but including structures in which parts are attached by or as mated connectors, fasteners, releasable self-fastening features, etc. The verb "to facilitate" is intended to mean "to make easier and/or less complicated", rather than "to enable".

Figure 1C:
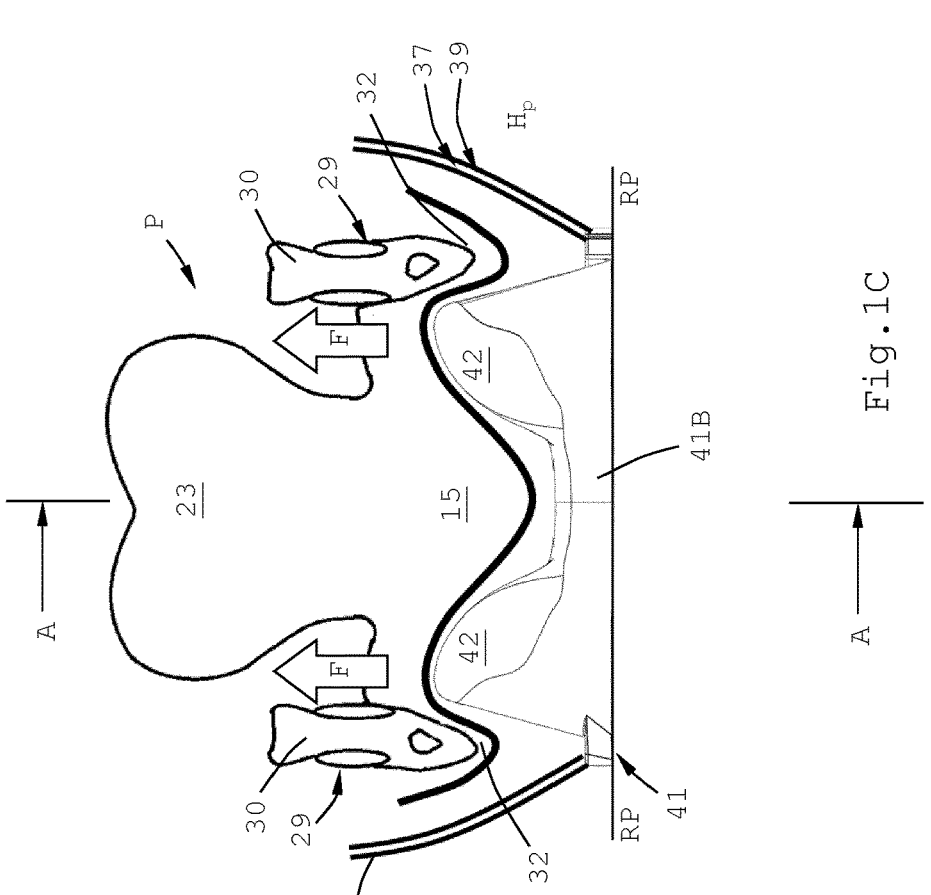
FIG. 1C is a partial schematic cross section, along plane BB indicated in FIG. 1A, of a human neck area also including part of a ventilation assembly as disclosed herein in operative position.
Figure 1B:
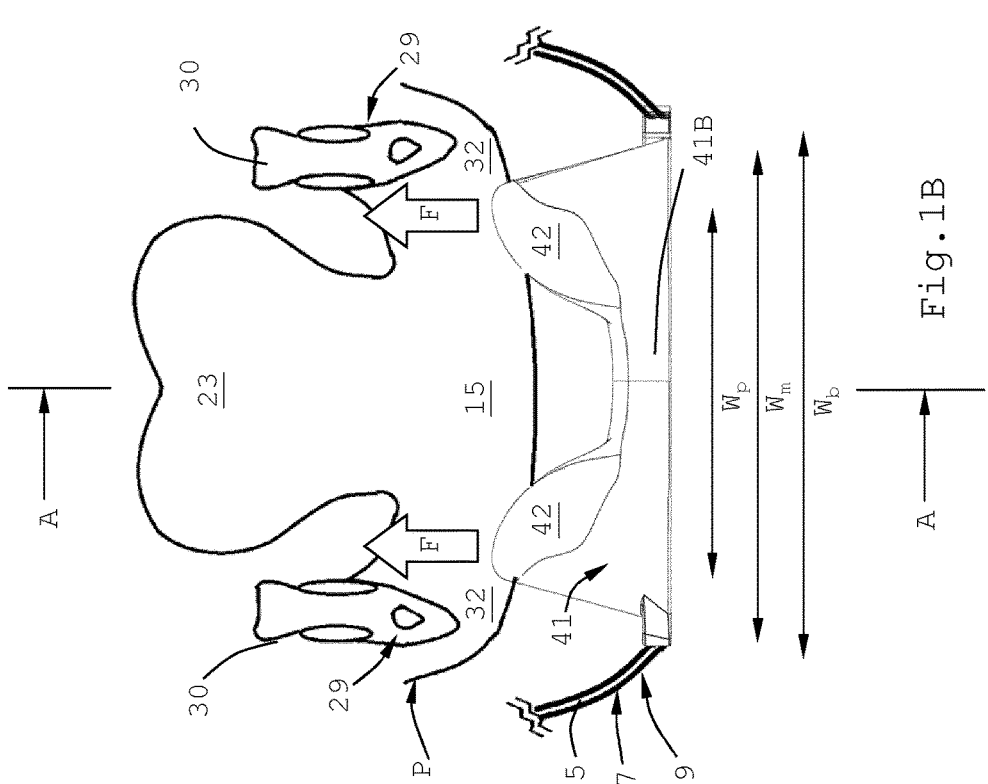
FIG. 1B is a partial schematic cross section, along plane BB indicated in FIG. 1A, of a human neck area also including part of a ventilation assembly as disclosed herein.
Figure 1D:
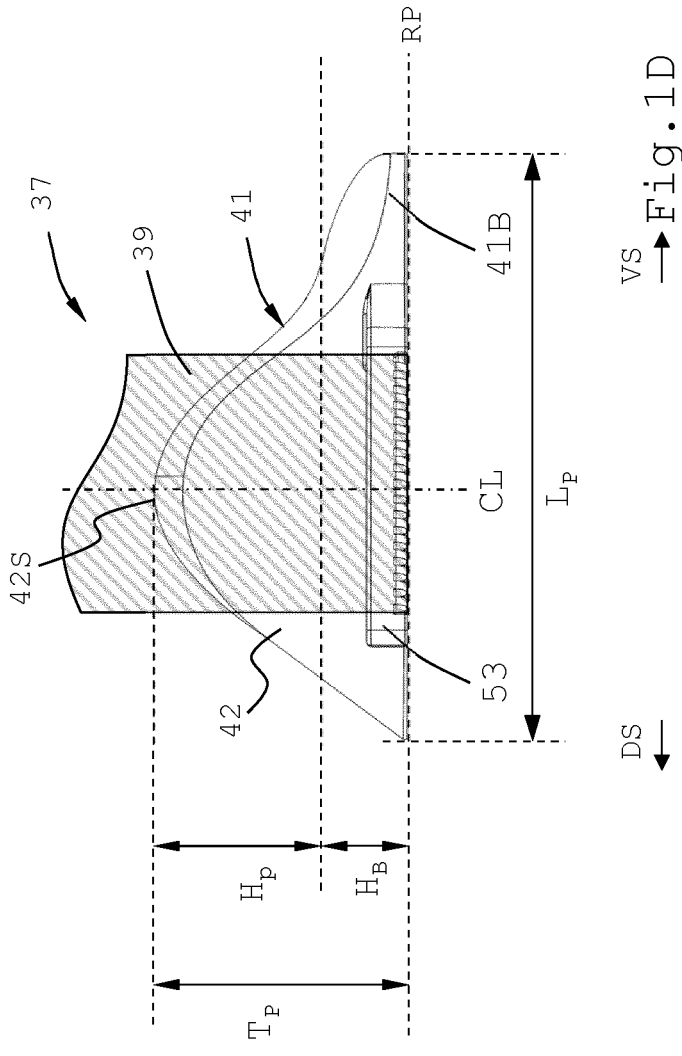
FIG. 1D is a partial side view of part of a ventilation assembly as disclosed herein.

FIGS. 1A-1C are partial schematic cross sections of a lower head and neck area of a person P, or: subject, according to sagittal plane AA (FIG. 1A, plane indicated in FIG. 1B and in FIG. 1C) and frontal plane BB (FIG. 1B, FIG. 1C, plane indicated in FIG. 1A). These figures (predominantly FIG. 1A) show the pharynx 1, larynx and trachea 3 of the subject P with a laryngeal mask 5 inserted in the airway (nose and/or mouth—pharynx—larynx—lungs) of the subject P in operative position. Discernible are the subject's nose 7, upper lip 9, lower lip 11, chin 13, floor of the mouth 15, and throat 17, as well as the back of the neck 19. Further are discernible the subject's palate 21, tongue 23, pharynx 1, epiglottis 25, laryngopharynx 26 and esophagus 27, as well as the mandible 29 with teeth 30 and the hyoid bone 31. Jaw tissue 32 (in particular gingivae) separates the soft tissue of the floor of the mouth 15 from the soft tissue of the subject's cheeks and mouth. The soft tissue of the floor of the mouth 15 is predominantly formed by the left and right submandibular triangles (trigonum submandibulare) and the submental triangle (trigonum submentale). The laryngeal mask 5, connected to a ventilation tube 33, is inserted in the laryngopharynx 26 in usual manner and covers the opening of the trachea 3. The laryngeal mask 5 comprises an inflatable cuff 35 for generally sealing off (the opening of) the trachea 3. Thus positioned and if properly fit, the patient subject P can be forcedly ventilated through the tube 33 connected to the mask 5.

Figure 2:
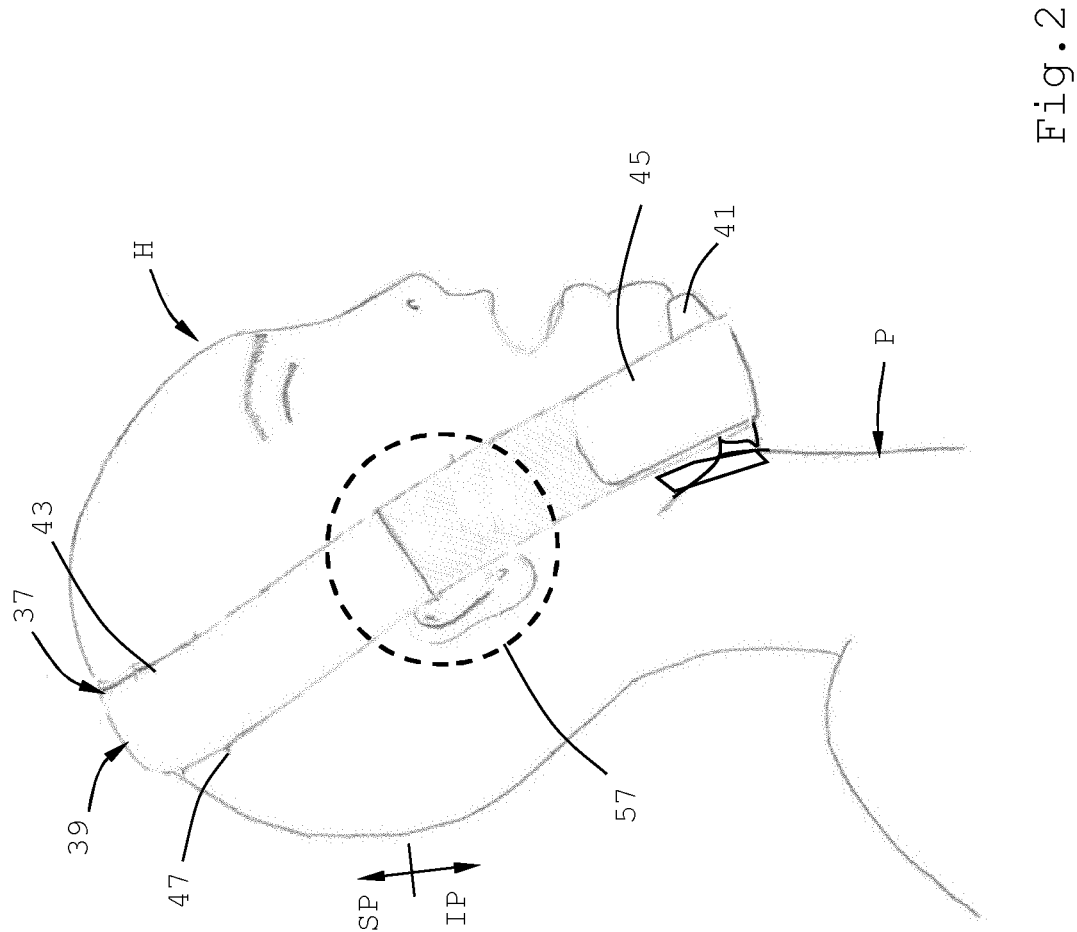
FIG. 2 is a side view of a subject wearing a ventilation assembly as disclosed herein.
Figure 3:
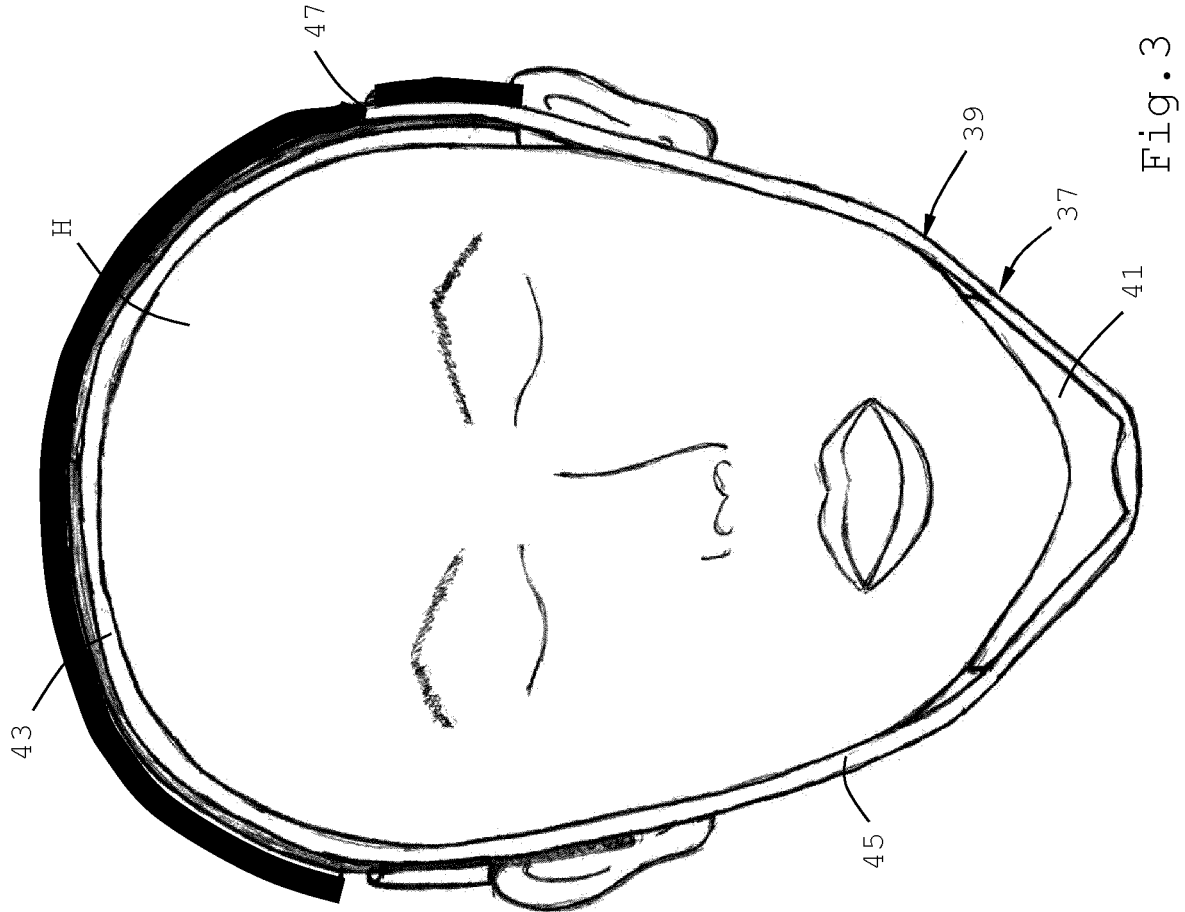
FIG. 3 is a front view of a subject wearing a ventilation assembly as disclosed herein.
Figure 4:
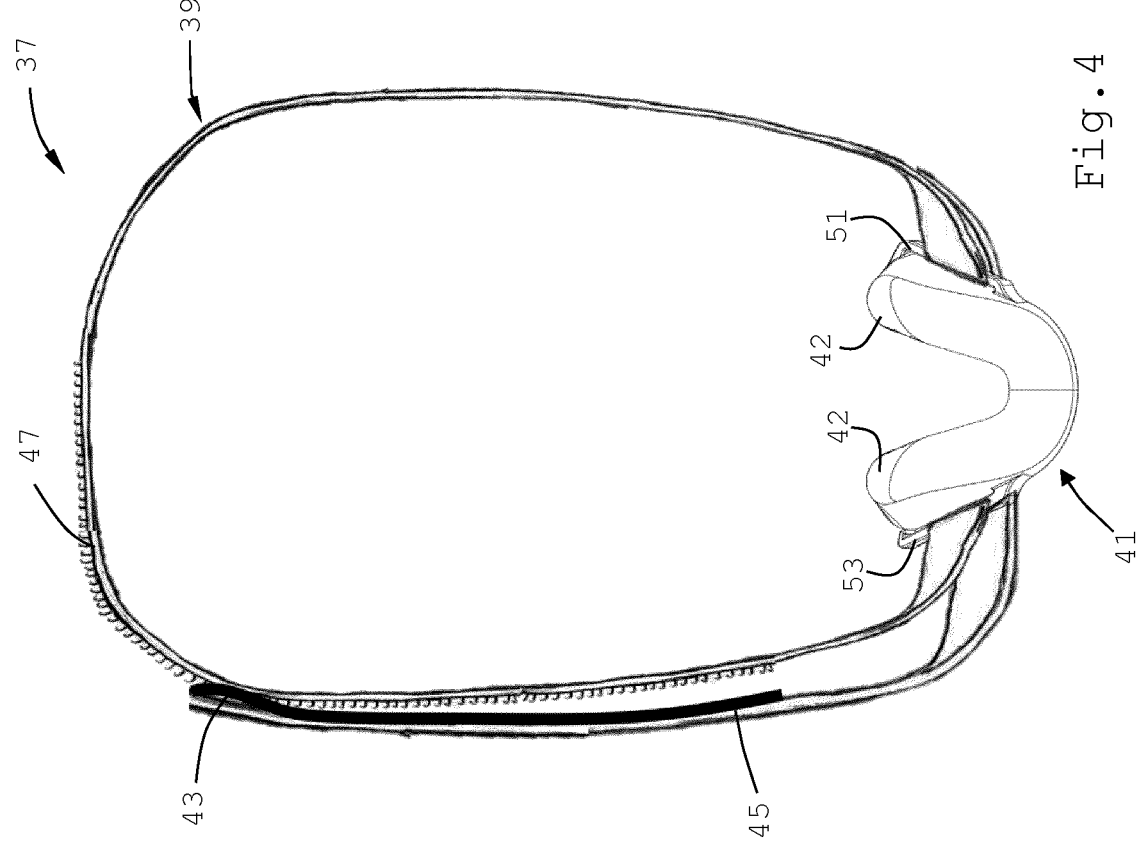
FIG. 4 is a front view of a ventilation assembly as disclosed herein.
Figures 5A, 5B, 6A, 6B:
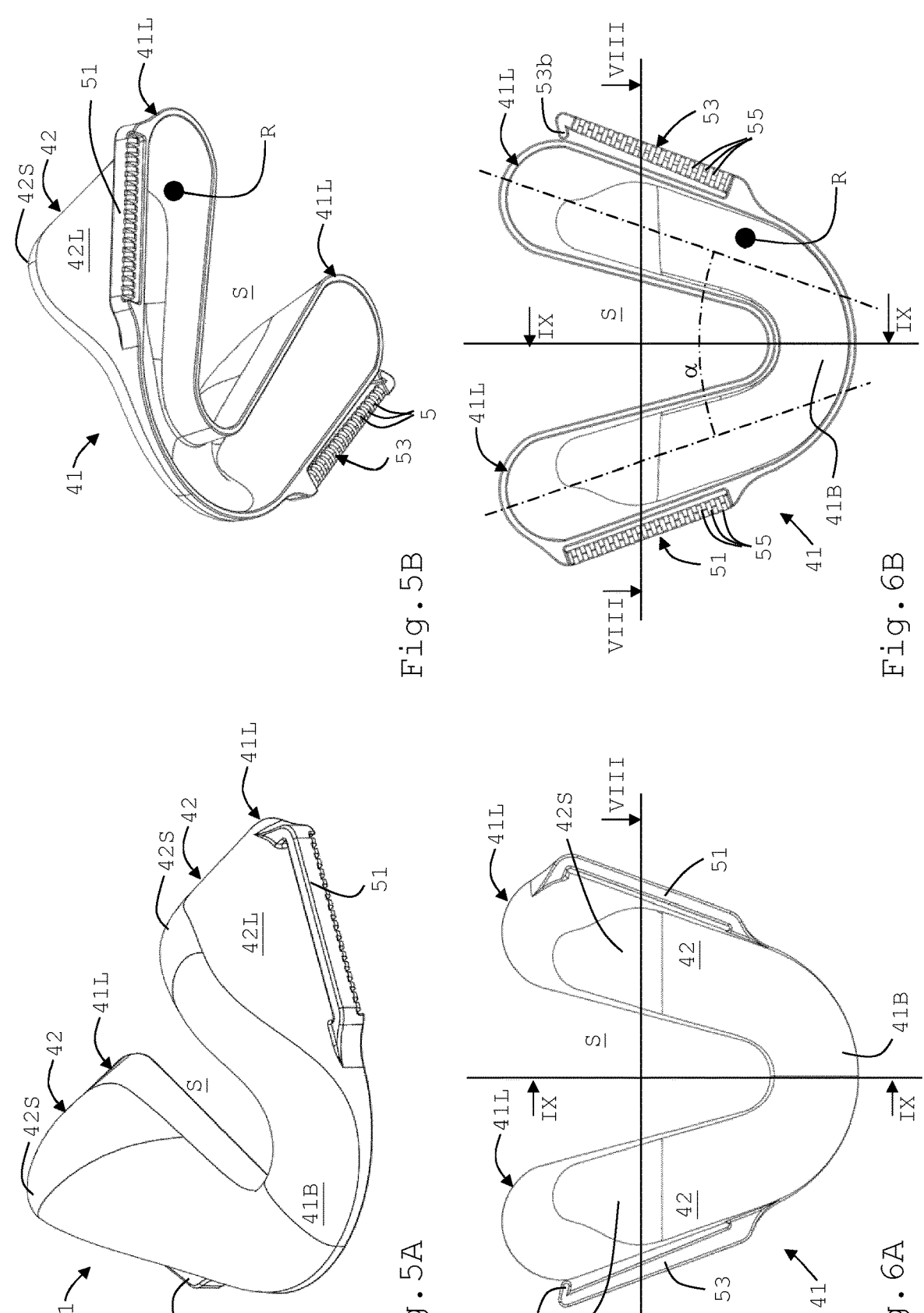
FIGS. 5A-5B are perspective views of the pusher from above and, respectively, below.
FIGS. 6A-6B are top and, respectively, bottom views of the pusher.

In order to reduce or prevent leaks in case of an otherwise improper sealing of the mask 5 in the laryngopharynx 26, the ventilation assembly 37 is provided, of which (use of) an embodiment is shown in FIGS. 2-4.

The ventilation assembly 37 comprises a head-wearable harness 39 and a pusher 41. Details of the pusher are shown in FIGS. 5A-9B. Note that all figures, in particular FIGS. 1A-4 are schematic and not to scale and that for clarity the ventilation assembly 37 is shown spaced from the subject's head; in operation the assembly will be in close contact with the skin and that displacements of tissue (see below) will be significantly smaller.

The shown harness 39 is formed as a single band but more complex harnesses may be used as well. The harness 39 is arrangeable on the head H of the subject P for supporting the pusher 41 against the floor of the mouth 15 of the subject P; see FIGS. 1A-1C and FIGS. 2-3. The pusher 41 comprises two laterally adjacent protrusions 42 in a cranial direction in use (as shown). The pusher 41 is arranged to displace soft tissue of the floor of the mouth 15 in cranial direction relative to the mandible 29 of the subject P, see arrows F in FIGS. 1A-1C. This force direction is generally in a parasagittal plane, inclined to the coronal direction generally from the floor of the mouth 15 to the subject's ear; the force direction preferably crosses the entrance (introitus) of the ear canal. However, in some cases the force direction may be across a rear (dorsal) half of the temple in front of (ventral of) the ear canal. Thus, when the laryngeal mask 5 is installed in the airway of the subject P as shown in FIG. 1A, the pusher 41 is arranged for urging internal soft tissue of the floor of the mouth 15 of the subject P, e.g. parts of the tongue 23 and/or epiglottis 25, against the laryngeal mask 5 in the airway of the subject P, without choking or otherwise impairing breathing of the subject P, and preferably without pressing the tongue against the intubation tube. As will be clear from FIGS. 1A-1C, due to the protrusions 42, the force F is locally larger near the mandible, at the submandibular triangles, than in between, at or near the submental triangle.

The direction of the force F may be such that the teeth 30 of the subject (in a normal healthy individual with average anatomic shape) are aligned in a normal biting position with the lower front teeth behind (i.e. dorsal of), but close to, the upper front teeth; no "overbite". The effect and the resulting position may be referred to as "jaw thrust". A so-called "chin-lift" position wherein the lower front teeth may pass and become positioned in front of (i.e. ventral to) the upper front teeth is considered best to be prevented.

The harness 39 comprises, here being substantially formed as, a flexible member, e.g. a band. The harness 39 may encircle, as shown, in use, the subject's head H generally in an anatomic coronal plane. The harness 39 may be closed and may comprise one or more elastic portions. The shown harness 39 comprises an optional fastener for size adjustment of the harness 39, e.g. a length adjustment of flexible members, such as hook-and-loop-type entanglement fasteners V e.g. such as commonly called "Velcro", in such case the hook-side should preferably be oriented outwardly, away from the subject's skin (FIG. 4). However, fasteners may take any suitable form or combination, e.g. comprising one or more of buckles, clasps, buttons, slides, zippers, D-ring fasteners, etc. In the shown harness, the band may have a varying width, e.g. comprising a relatively broad portion 47 for arranging on the top of the subject's and head narrower portions 43, 45 connectable or connected to the pusher; see FIGS. 10A-10B.

As will be clear from FIGS. 1A-4, the ventilation assembly requires little space below the chin and does not interfere with access to the chest and/or the neck areas. E.g. the (pusher 41 of the) assembly 37 may be arranged above (cranial of) the thyroid (cartilago thyroidea), as shown, and possibly even above (cranial of) the hyoid. Such assembly also keeps the neck area accessible for (emergency) tracheotomy.

As most clearly visible in FIG. 4, and FIGS. 5A-9B the pusher 41 may be generally U-shaped in transverse direction, having a bridge 41B at a front side (in use: ventral side VS—FIG. 1D) and opposing legs 41L at a rear side (in use: dorsal side DS—FIG. 1D), each leg 41L comprising a protrusion 42. The protrusions have a summit 42S. The protrusions are separated by a space S. Preferably the pusher 41 is symmetric with respect to the sagittal plane, as shown. Thus, in situ under a subject's lower jaw, part of the subject's throat, in particular the trigonum submentale, can be accommodated in space S of the pusher 41.

Best seen in FIGS. 1A, 5B,6B, 8B, 9B, the pusher 41 is hollow accommodating operator's fingers OF in each protrusion 42 (schematically indicated in FIG. 8B). In particular, the shown pusher 41 is formed as a hollow shell, as options being single walled and providing a continuous recess R. As an option, the pusher 41 has a substantially constant wall thickness (FIGS. 8B, 9B). However, one or more fortifying ribs may be provided in the recess R; it is preferred that the pusher is shape-maintaining in normal use and operation, deforming less than 10%, preferably less than 5% more preferably less than 3% under load in appropriate use (operably supported by the harness and applying the force F to the extent not interrupting blood flow in, and/or otherwise harming, the subject's tissue) compared to an unloaded situation. By accommodating the operator's fingers OF in one or more protrusions 42 and/or the bridge 41B, placement and/or adjustment of the pusher 41 and the assembly as a whole may be simplified.

Further, as best seen in side view (FIGS. 1A, 1D and 9A and cross section view 9B), the bridge 41B may have a small height $H_B$. Also, the bridge 41B may have a short length $L_B$ in the sagittal plane (see FIG. 9B), e.g. a front side of the pusher 41. Each leg 41L may form a protrusion 42 in general cranial direction relative to the bridge 41B having a height $H_P$ above the bridge 41B and a total height $T_P=H_P+H_B$.

The bridge 41B may extend for a length $L_B$ of less than ½ a sagittal length $L_P$ of the pusher 41, e.g. less than ¼ or between about ⅓ and ⅕, e.g. about ¼, from the front side of the pusher 41. The protrusions 42, in particular the summits 42S thereof, are arranged dorsal of the bridge 41B.

The protrusions 42 of the pusher 41 are, and preferably the entire pusher 41 is, at least on a side to face the subject, smoothly rounded. The protrusions 42 may be generally bulging upward (in use: in cranial direction). The summit 42S may be in a position between about ⅓ and ½ from the dorsal side of the pusher 41, in particular between ⅖ and ½ from the dorsal side, here being between about ½ and ⅔ from the frontal/ventral side of the pusher 41, in particular between ½ and ⅗ from the dorsal side.

Best seen in FIGS. 1B-1C and 7A-8B, the protrusions 42 provide the space S with a shape generally flaring in cranial direction. The protrusions 42 have a generally smoothly laterally outwardly curved medial side 42M and a generally steep lateral face 42L. Each summit 42S is laterally outward on the respective leg 41L for less than about ¼ of the sagittal cross sectional width of the leg 41L, preferably in a range of about ⅕ to ¹⁄₁₀ of the sagittal cross sectional width of the leg 41L, as shown. E.g. a leg may have a width of ab A smoothly curved shape of the protrusion 42 may reduce local pressure against the floor of the mouth and, at a dorsal side, the throat, and may reduce or prevent possible discomfort and/or complications associated with elevated pressure, such as poor or stopped blood perfusion of tissue portions. It is further noted that the relatively small thickness $H_B$ of the bridge 41B of the pusher 41 may reduce local pressure against the mandible and the soft tissue of the front part of the submental triangle and/or the chin, and thus possible associated discomfort and/or complications may be prevented. The combination of a U-shape and a relatively high protrusion summits assists providing a locally elevated pressure at the floor of the mouth, in particular at the submandibular triangles and less so on the submental triangle, while reducing or preventing elevated pressure on the throat and airway.

To displace the soft tissue relative to (the angle and/or body of) the subject's mandible 29, the pusher 41 is formed so as to fit at least partly inside the subject's mandible 29, in particular fitting at least partly between the subject's left and right angles, or: bodies, of the mandible 29, so as to deform the subject's floor of the mouth 15 in accordance with the shape and deformability thereof and the shape of the subject's—mandible 29; see FIGS. 1B-1C.

As shown, the protruding height of the protrusion 42 of the pusher 41 may vary continuously and smoothly and/or being in accordance with the deformability of the floor of the mouth 15 against the mandible 29 (which narrows from the angles towards the chin), so as to prevent excessive stress and/or pressure in the respective tissue portions, notably each trigonum submandibulare.

Note further that the pusher may occupy a small volume below the floor of the mouth. The size of the pusher 41, in particular the protruding height $H_P$ and/or dorsal thickness $T_D$ of the pusher may be chosen such that the assembly, in use, is arranged above (cranial to) the subject's thyroid, e.g. see FIGS. 1A, 3, 6-8.

The pusher may have a length $L_B$ with respect to the sagittal plane (see FIG. 9B) in a range of about 55-85 mm, preferably in a range of about 65-80 mm, most preferably in a range of about 70-75 mm. The bridge may have a length $L_B$ in the sagittal plane (see FIG. 9B) in a range of about 10-35 mm, preferably in a range of about 15-30 mm, most preferably in a range of about 20-25 mm. The legs may have a width in a coronal plane (see FIG. 8B) in a range of about 20-35 mm, preferably in a range of about 25-30 mm. The opening angle α of the legs (see FIG. 6B) may be in a range of about 35-50 degrees, preferably in a range of about 37-45 degrees, most preferably in a range of about 40-43 degrees (see FIGS. 6A-6B) The pusher may have a total height $T_P$ determined by the summit and the bridge have a bridge height $H_B$ and, the bridge height $H_B$ to total height $T_P$ respectively, may be in a ratio of about $H_B{:}T_P{=}1{:}3{-}2{:}3$. E.g. The bridge may have a height $H_B$ in the sagittal plane (see FIG. 9B) in a range of about 10-35 mm, preferably in a range of about 15-30 mm, most preferably in a range of about 20-25 mm.

The pusher may have total height TP with respect to the sagittal plane in a range of 20-45 mm, in particular 25-35 mm, more in particular 30-35 mm. A higher (or: "thicker") pusher may obstruct access to the throat of the subject, a lower (or: "thinner") pusher may hinder providing and/or determining a suitable pressure onto the floor of the mouth.

The protrusion summit may have a height HP above the bridge (see FIGS. 9A-9B) in a range of about 5-25 mm, preferably in a range of about 7-20 mm, most preferably in a range of about 10-15 mm. Such elevations tend to provide tissue displacement for most persons suitable for providing the desired sealing effect; an elevation in a range 10-12 mm may be optimal. One or each protrusion may have a full width at half maximum height in plane through the summit longitudinal direction along the leg (see dash-dotted lines in FIG. 6B) in a range of about 35-55 mm, preferably in a range of about 40-50 mm, and may have a full width at half maximum height through the summit in a coronal plane (see FIG. 8B) in a range of about 20-30 mm, preferably in a range of about 23-27 mm, accommodating human adult fingers of a care giver and preventing excessive local forces to subject. A lateral separation $S_P$ of the summits 42S of the protrusions 42 of the pusher 41 may be in a range of about 65-80 mm, preferably in a range of about 70-75 mm. Such width tends to fit most human adolescents and adults.

The pusher 41 may be provided as a separate part which may be positioned against the subject P and kept in place by the harness 39, but preferably the pusher 41 is attached to the harness 39.

Best seen in FIGS. 1D, 4-9B, the pusher is provided with connectors 51, 53 on lateral outsides of the legs 41L for operably connecting the harness 39 and the pusher. Here, one connector 51 is formed as a closed loop and one connector 53 is formed as a hook (here optionally comprising a barb 53b). However, two or more connectors may be the same, e.g. the pusher being provided with two hooks like hook 53. The connectors 51, 53, are optionally provided with teeth 55 or corrugations etc. to retain at least part of the harness 39 in a desired position. As visible in FIG. 4, the harness 39 may be looped about the connectors 51. The teeth 55 may be, as shown, discoid, being rounded in one direction with a large radius, in particular in circumferential direction in accordance with the wrapping to allow smooth sliding over the teeth facilitating length adjustment of the harness. In a perpendicular direction the teeth may have a small radius and/or be sharp to provide friction to the harness loop.

Thus, connectors comprise a support portion elongated along an axis for operably engaging the harness circumferentially looped around the support portion, the support portion being provided with plural axial corrugations, e.g. castellations, forming circumferentially rounded teeth.

The harness 39 may be attached to the pusher 41 permanently or temporarily. The connectors 51, 53 being positioned on the steep lateral walls 42L facilitates providing the force F in a direction generally along the wall 42L. This helps orienting the force F in a desired direction, and largely along the mandible (e.g. see FIGS. 1B-1C). It also helps preventing deformation of the pusher 41 in use.

Further, the connectors 51, 53 may define a reference plane RP. In the shown embodiment the reference plane RP is parallel to a bottom of the pusher 41. The connectors 51, 52 may be arranged, as shown (see in particular FIG. 1D), such that the harness is configured to provide a force substantially symmetric in a sagittal plane relative to the summit 42S and a tangent plane to the summit 42S parallel to the reference plane RP. E.g. in FIG. 1D a centre line CL is indicated, being normal to a tangent plane to the summit 42S and to the reference plane RP, and the harness 39 is arranged symmetric about the centre line CL. This facilitates directing the force F in a sagittal plane by orienting the harness more ventral or dorsal about the subject's head, in particular in case of a harness having a single band the force direction will then generally be along the band. A band having a width in a range of about 20-35 mm, preferably in a range of about 25-30 mm, may facilitate directing the pusher and prevent local pressure on the subject's skin.

Figure 10A:
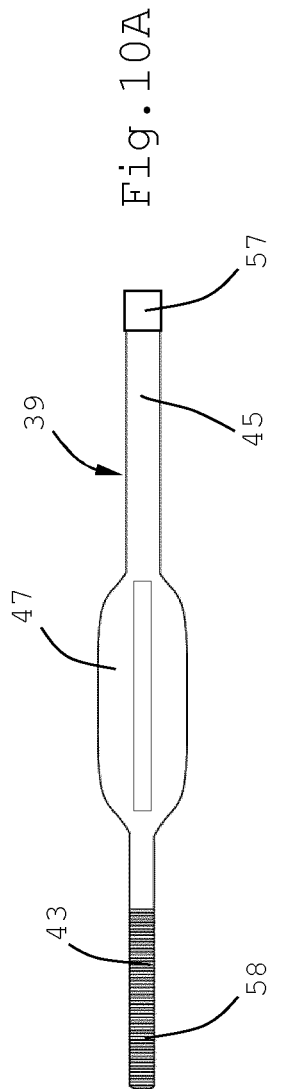
FIGS. 10A-10B show an embodiment of a harness.
Figure 10B:
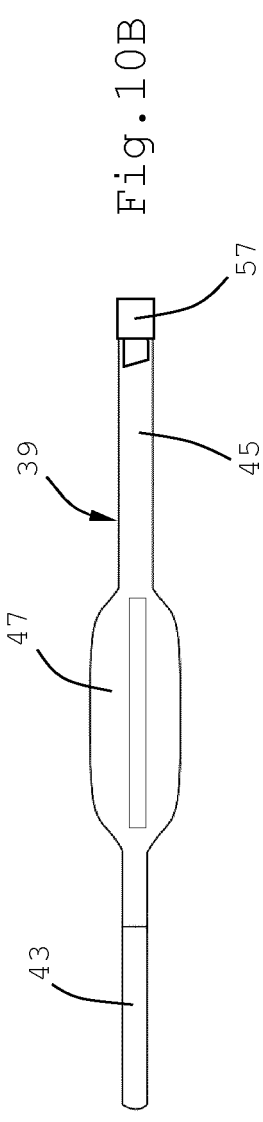

In FIGS. 10A, 10B, is shown as an exemplary embodiment of a head wearable harness 39 a head band may be provided having relatively narrow end portions 43, 45 with a widened portion 47 in between. On one end a loop 57 may be provided which may be permanently attached to the pusher 41 or be fit about a hook (e.g. hook 53). Also or alternatively, an end 43 may be provided with a closure 58, e.g. an entanglement-type closure such as Velcro or other connector allow continuous adjustment of a length of the head band.

In FIG. 2 is schematically indicated that, as an option, one or more sound mufflers 57 and/or sound emitters for controlling sound to an ear of the subject may be provided to the harness 39.

The disclosure is not restricted to the above-described embodiments which can be varied in a number of ways within the scope of the claims. For instance the pusher and/or the harness may be shaped differently. Relative sizes of portions of the assembly may differ. The harness and/or pusher may be associated and/or connected with other devices; e.g. the harness and/or pusher may support one or more sensors attached to an/or embedded in the harness and/or pusher, respectively.

Elements and aspects discussed for or in relation with a particular embodiment may be suitably combined with elements and aspects of other embodiments, unless explicitly stated otherwise.

The invention claimed is:

1. A ventilation assembly for use in ventilation of a subject using a laryngeal mask comprising a head-wearable harness and a pusher, wherein the head-wearable harness is arrangeable on a head of the subject for supporting the pusher to press against the floor of the mouth of the subject, the pusher is generally U-shaped in a transverse direction, comprising a bridge in a front portion for, in use and operably supported by the head-wearable harness on the subject, accommodating a tissue located at a submental triangle of the subject, and laterally opposing legs extending rearward from the bridge in a rear portion, wherein the bridge extends for ⅓ to ¼ of a pusher length from a front end of the pusher;

the legs comprise laterally opposite protrusions arranged in a position dorsal to the bridge and wherein the protrusions provide a space between them having a shape generally flaring in a cranial direction in use to displace, in use and operably supported by the harness on the subject, soft tissue of the subject at a left and a right submandibular triangles in the cranial direction relative to a mandible of the subject and surrounding tissue of the subject's the submental triangle, when the laryngeal mask is installed in an airway of the subject, urging internal soft tissue of the subject against the laryngeal mask in the airway of the subject, and each protrusion is hollow providing a recess at a bottom side of the pusher, for accommodating an operators' finger so as to facilitate manipulation and placement of the pusher.

2. The ventilation assembly according to claim 1, wherein the pusher is formed as a continuous hollow body, and/or wherein the pusher has a substantially constant thickness in a direction normal to an outside surface of the pusher.

3. The ventilation assembly according to claim 1, wherein the bridge and the protrusions provide a substantially continuously smooth surface, the bridge having a saddle shape.

4. The ventilation assembly according to claim 1, wherein when the ventilation assembly is in use, the protrusions each have a summit in a range arranged from a rear end of the pusher between ⅓ and ½ of a pusher length.

5. The ventilation assembly according to claim 1, wherein the pusher has a length with respect to a sagittal plane in a range of 55-85 mm; and/or a total height with respect to the sagittal plane in a range of 20-45 mm.

6. The ventilation assembly according to claim 1, wherein each protrusion has a base and each protrusion having a summit laterally outward on a respective said base, being arranged in a lateral outer half of the respective base.

7. The ventilation assembly according to claim 1, comprising one or more connectors for operably connecting the head-wearable harness and the pusher.

8. The ventilation assembly according to claim 7, wherein the one or more connectors comprise at least one hook and/or at least one loop for operably engaging the head-wearable harness.

9. The ventilation assembly according to claim 8, wherein the at least one hook and/or the at least one loop comprises a support portion elongated along an axis for operably engaging the head-wearable harness circumferentially looped around the support portion, the support portion being provided with plural axial corrugations.

10. The ventilation assembly according to claim 1, wherein the head-wearable harness is attachable or attached such that when in use, the head-wearable harness is arranged laterally adjacent a summit of each protrusion.

11. The ventilation assembly according to claim 1, wherein the harness comprises a flexible band.

12. The ventilation assembly according to claim 1, comprising one or more sound mufflers and/or sound emitters for controlling sound to an ear of the subject.

13. An assembly, comprising the ventilation assembly according to claim 1 and a laryngeal mask.

\* \* \* \* \*